United States Patent [19]

Poley

[11] Patent Number: 4,917,680
[45] Date of Patent: Apr. 17, 1990

[54] FOLDED INTRAOCULAR LENS WITH ENDLESS BAND RETAINER

[76] Inventor: Brooks J. Poley, 2 Greenway Gables, Minneapolis, Minn. 55403

[21] Appl. No.: 345,837

[22] Filed: May 1, 1989

Related U.S. Application Data

[63] Continuation-in-part of Ser. No. 213,325, Jun. 30, 1988, which is a continuation-in-part of Ser. No. 31,250, Mar. 26, 1987, Pat. No. 4,769,034.

[51] Int. Cl.⁴ .............................................. A61F 2/16
[52] U.S. Cl. ......................................................... 623/6
[58] Field of Search ............................................. 623/6

[56] References Cited

U.S. PATENT DOCUMENTS

| | | | |
|---|---|---|---|
| 4,527,294 | 7/1985 | Heslin | 623/6 |
| 4,573,998 | 3/1986 | Mazzocco | 623/6 |
| 4,605,409 | 8/1986 | Helman | 623/6 |
| 4,681,102 | 7/1987 | Bartell | 623/6 |
| 4,769,034 | 9/1988 | Poley | 623/6 |

OTHER PUBLICATIONS

"Soft IOL Technology: the New Frontier" by V. L. Bohn, Ocular Surgery News, vol. 5, No. 5, 3/1/87.

Primary Examiner—Richard J. Apley
Assistant Examiner—James Prizant
Attorney, Agent, or Firm—Wood, Herron & Evans

[57] ABSTRACT

A resilient intraocular lens, folded on itself to reduce its transverse dimension for implanting, is releasably held in the folded configuration by a retainer in the form of a pliable, severable band which extends circumferentially around the lens. Preferably the retainer is securable by a pull strip along a line of weakness, to permit the lens to unfold. The pull strip remains attached to the retainer for removing it from the eye after the lens has been released.

11 Claims, 1 Drawing Sheet

FOLDED INTRAOCULAR LENS WITH ENDLESS BAND RETAINER

RELATED APPLICATION

This application is a continuation-in-part of my co-pending application Ser. No. 213,325, filed June 30, 1988, titled "Foldable Intraocular Lens and Improved Fold Retaining Means," which is a continuation-in-part of application Ser. No. 07/031,250, filed Mar. 26, 1987 and now U.S. Pat. No. 4,769,034.

Field of the Invention

This invention relates generally to the implantation of intraocular lenses, and more specifically to a lens which is held in a folded configuration for implanting, by an endless band-like retainer around it.

BACKGROUND

The use of intraocular implant lenses has been highly developed in recent years, especially in connection with the removal of cataracts, and such operations are now common medical procedure. In such procedures it is desirable to minimize the size of the incision which must be made to insert and position the lens in the eye, in order to shorten the time required for healing and to minimize any chance of wound failure.

Most previous implanting techniques have required that the incision made in the eye be slightly wider than the diameter of the lens to be implanted so that the lens can be inserted through the incision. Recently techniques have been developed for reducing the width of certain lenses prior to incision, by folding or rolling prior to insertion, see V.L. Bohn, "Soft IOL Technology", *Ocular Surgery News*, Volume 5, No. 5, Mar. 1, 1987, page 1.

My U.S. Pat. No. 4,769,034, titled "Folded Intraocular Lens, Method of Implanting Folded Intraocular Lens", discloses a resilient lens which is retained in folded configuration for implanting, by a retainer wrapped partway around the lens and held in place as by ties between its ends.

My copending application Ser. No. 213,325, previously referred to, discloses a folded lens which is held folded by fastening means which are integral with the lens itself, or alternatively by sutures which extend through apertures in overlying parts of the folded lens.

The techniques for forming and securing the foregoing retaining means are relatively complicated, involving securing a retainer around the lens, or suturing through the folded lens, or forming the retainer integrally with the lens.

SUMMARY OF THE INVENTION

It has been the purpose of this invention to provide a folded lens retainer which can more easily be applied to the lens, and which can more easily be removed from around the lens, in situ within the eye.

In accordance with this invention, the retainer is in the form of a pliant endless band or loop which snugly encircles the folded lens. The retainer is removed from the lens by tearing, slitting or otherwise severing it transversely. Preferably, a line of weakness is provided across the retainer to facilitate severing it within the eye. This line may be defined by a series of perforations or by a relatively thinner web portion, along which the retainer will tear or sever more easily.

The provision of a line of weakness facilitates tearing or severing of the retainer, but is not absolutely necessary. If no line of weakness is provided, the retainer can be severed with a scalpel along the gap o space between the overlying edges of the folded lens.

A "pull strip" is provided to facilitate removal of the retainer from the eye after the lens has been released. The pull strip is preferably secured to the retainer like the tear strip around a package of crackers, and shears it transversely when pulled.

The retainer can be preformed as an endless loop which is slipped endwise over a folded lens. It is contemplated that the retainer may be of a heat shrinkable material so that it can be slightly "shrunk" around the lens to hold it securely. Alternatively, the retainer may be wrapped around a folded lens and its ends secured, to form a loop.

DESCRIPTION OF THE DRAWINGS

The invention can best be further described by reference to the accompanying drawings, in which.

DETAILED DESCRIPTION

Figure 1:
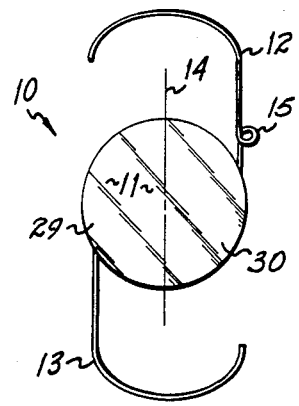
FIG. 1 is a plan view of one type of foldable lens with which the invention can be used, showing the lens in its unfolded condition.

The invention can be utilized with existing types of foldable lenses, one of which, designated by 10, is shown for illustrative purposes in FIG. 1. The lens has a generally circular optical or "active" area 11, with filamentary, springlike haptics 12 and 13 which extend oppositely from the optical area 11. The lens is made of resiliently foldable material and is foldable in half around an imaginary axis of folding designated by dashed line 14. Foldable lenses are generally known in the art and hence are not further described herein.

Figure 2:
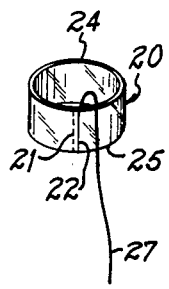
FIG. 2 is a perspective view of the preferred type of endless band retainer.
Figure 3:
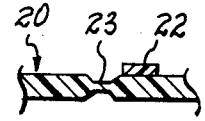
FIG. 3 is an enlarged cross-section of a portion of an alternative form of retainer having a "thinned" line of weakness.

The preferred form of releasable retainer 20 for holding the lens in folded configuration is an endless band or sleeve (FIG. 2). It may be a segment of an extrusion of pliant flexible material such as cellophane, saran, or polyethylene, and is sufficiently thin and fragile to be severable in the eye a by tearing or by slitting with a scalpel. The retainer 20 preferably has a line of weakness, indicated at 21, which in the embodiment shown comprises a series of spaced slits or perforations. Alternatively, as shown in FIG. 3, the line of weakness may comprise a relatively thin unperforated web portion 23, which can be cut or torn. A pull or tear strip 22 is adhesively secured to the retainer 20, preferably transversely across it between circumferential edge 24 (which is at the top as viewed in FIG. 2) and the lower circumferential edge 25. This pull strip 22 functions like the pull strip commonly provided around the wrappers of packages of crackers or gum. It is adhesively secured to band 20 closely adjacent the desired tear line 21, and concentrates the stress on the band in the area closely adjacent to line 21 so that the retainer tears preferentially along that line. It is preferred that the pull strip 22 extend upwardly from lower edge 25 to top edge 24 (i.e., that edge which is innermost in the eye when the lens is being implanted), and that its tail 27 fold over and return unsecured across the retainer, past the lower (outermost) edge. With this arrangement a gentle pull on tail 27 while the lens is held adjacent top edge 24, will exert a severing or shearing stress across the retainer along the line adjacent the pull strip. The pull strip remains attached to the retainer after the retainer has been parted, and (as further explained below) can then be used to draw the retainer carefully from the eye.

Figure 4:
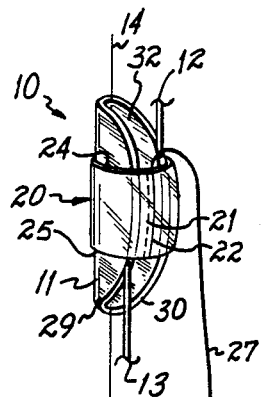
FIG. 4 is a perspective view showing a folded lens with a retainer in place around it.

As shown in FIG. 4, prior to implanting lens 10 is folded in half along axis of folding 14 so that its overlying halves or portions 29 and 30 are facially opposed with their edges overlying and adjacent. Retainer 20 is slipped over the lens to encircle it, with circumferential edges 24 and 25 being generally transverse (perpendicular) to the lens axis of folding 14. Haptics 12 and 13 extend in opposite directions from the retainer. Tail 27 of pull strip 22 is of sufficient length that it can trail outside the eye for removing the retainer after the lens has been released and unfolded.

The line of weakness 21 and pull strip 22 are preferably oriented along the "gap", i.e., the space 32 between the two lens halves 29, 30. Even if no line of weakness is provided, with pull strip 22 so oriented, it is easier to hold the lens (FIG. 7) for pulling tail 27. Alternatively, the retainer can be slit along the gap with a small scalpel without minimum danger of the cutting edge contacting or nicking the lens surface.

In order to place the endless sleeve 20 of the type shown in FIG. 2, around the lens 10, the lens is first folded and the retainer is slipped endwise around it, like a napkin ring. Gap 32 can be "pinched" to accommodate the retainer, or the retainer may be elastic or may be heat shrunk to a smaller size. In either case retainer 20 must not fit so tightly that it "creases" the lens along the axis of folding, nor so loosely that it slides off the curved edges of the lens during handling or implanting. It is contemplated that the lens can be supplied by the manufacturer folded and with the retainer in place. However, since a folded lens may tend to take a "set" or crease if left folded too long a time before use, the lens can be supplied unfolded, and then folded and the retainer applied by the physician at the time of implant.

Figure 7:
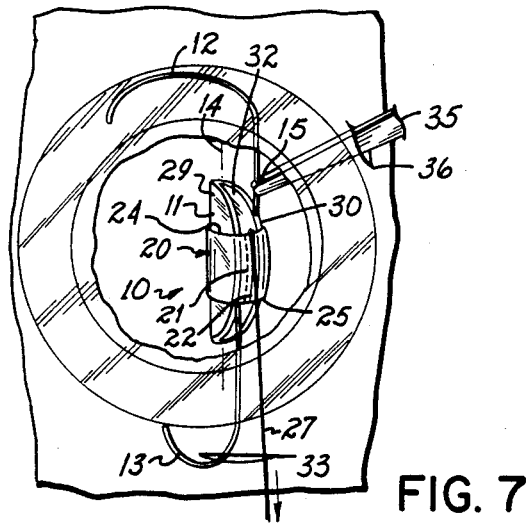
FIG. 7 illustrates the preferred technique by which the lens, once inserted into the eye, is held while the pull strip is pulled to sever the retainer.

The lens with the retainer around it may be implanted and released by a "two incision" technique such as shown in FIG. 7 and described in detail in my patent No. 4,769,034. Briefly, a primary incision 33 is formed, having a width sufficient to accommodate the "half" width of the folded lens, for example about 3.2 mm for a lens of 6.5 mm diameter. The lens is slipped through the primary incision in a direction generally parallel to the axis of folding 14 and is moved into the lens cavity. The upper (right) haptic 12 is then gripped, as by a tweezer 35 which is inserted through a secondary incision 36 angularly displaced from the primary incision 33. (Alternatively, as shown in FIG. 1, one haptic 12 may have a gripping means on it in the form of a loop 15, adjacent the lens, whereby it can be held by a hooked instrument while the pull strip is pulled.) The tail 27 of strip 22 extends out through primary incision 33. When pulled it causes the retainer to tear or part adjacent to it. As this is done, the lens is held inwardly in the eye, i.e., away from the cornea, so that the upper or anterior lens half 29 will not abrade the cornea while the lens unfolds. Unfolding can be controlled by instrument 35 inserted through the secondary incision, as described in greater detail in my patent No. 4,769,034. Once the lens has unfolded, the retainer, which will then be on the interior side of the lens, is removed through the primary incision by gently pulling tail 27.

Figure 5:
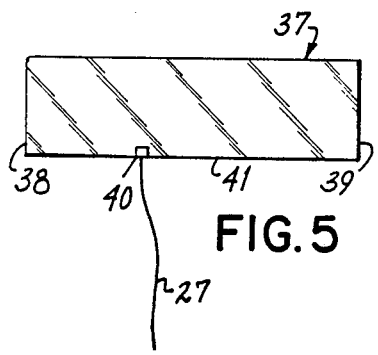
FIG. 5 is a plan view of an alternative form of retainer, before its ends are secured.
Figure 6:
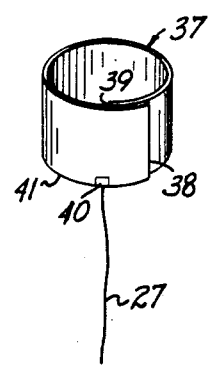
FIG. 6 is a perspective view of a retainer formed from the blank shown in FIG. 5.

In the embodiment of FIG. 2, the retainer 20 is in the form of an endless band, and is slipped endwise onto the lens 10. In FIGS. 5 and 6 an alternative embodiment is shown which differs in two respects. It is formed initially as a flat rectangular blank 37 having ends 38 and 39, and is made into a band by placing its ends in overlapping relation (shown in FIG. 6) and securing them together, either on or off the lens 10. The ends 38 and 39 are secured by an adhesive that does not affect eye tissue or fluids.

The embodiment of FIGS. 5 and 6 further differs in that it has no preformed line of weakness. Pull strip 27 does not extend across the band, but rather is adhered only at an end 40 adjacent the lower edge 41. The pull strip 27 does not of itself sever this retainer; it is intended to be slit by a scalpel. The function of pull strip 27 in this embodiment is to draw the retainer out of the incision after it has been severed.

From the foregoing it will be seen that this invention provides a simplified form of retainer which may more easily be placed around a lens by the manufacturer or by the physician at a time just prior to implant. The retainer does not require the provision of an integral latch or other attaching means on the lens itself; nor does it require forming of apertures for suturing through the lens.

As used herein the term "folded" is meant to include a single fold as shown in FIG. 4, or multiple folds around two or more parallel axes of folding, or a lens which is rolled up on itself. The invention is applicable to all such folded lenses, the width of which is reduced for insertion.

Having described the invention, what is claimed is:

1. A resilient intraocular lens which is folded on itself along an axis of folding so as to reduce its transverse dimension and thereby enable it to be implanted in an eye through a smaller incision than would otherwise be required, and a releasable retainer which extends circumferentially around the lens to retain it so folded while being inserted in the eye, said retainer comprising a band of pliant severable material, said band having opposite circumferential edges, said retainer surrounding the lens with said edges transverse to said axis of folding, said retainer having means forming a line of weakness extending from one said circumferential edge of the band, across the band to the other of said circumferential edges, said retainer being severable along said line of weakness thereby to permit the lens to be unfolded within the eye.

2. The lens and retainer of claim 1 wherein a pull strip is attached to said retainer adjacent said line of weakness, said pull strip being adapted to tear the retainer along said line of weakness when pulled.

3. The lens and retainer of claim 2 wherein said pull strip is secured to said retainer to remain attached to the retainer after the retainer has been severed.

4. The lens and retainer of claim 3 wherein said pull strip is attached to said retainer across it from one said edge to the other, and wherein said pull strip has an elongated tail by which the retainer can be withdrawn from the eye after the lens has been released, said tail overlying said retainer and extending across it from said other edge and past said one edge.

5. The lens and retainer of claim 1 wherein said line of weakness is defined by a series of spaced perforations.

6. The lens and retainer of claim 1 wherein said retainer is a band of stretchable material and said lens tensions the retainer around it.

7. The lens and retainer of claim 1 wherein said retainer is a strip having ends which are secured together to form said band.

8. The lens and retainer of claim 1 wherein said retainer is a band of heat shrinkable material, and is heat shrunk around the lens.

9. The lens and retainer of claim 1 further wherein a pair of haptics are mounted to the lens, the said haptics extending in opposite directions from the lens and the retainer.

10. The lens and retainer of claim 9 wherein at least one haptic has a gripping means adjacent the lens, whereby it can be held while said retainer is being severed along said line of weakness.

11. A resilient intraocular lens which is folded on itself along an axis of folding so as to reduce its transverse dimension and thereby enable it to be implanted in an eye through a smaller incision than would otherwise be required, and a releasable retainer which extends circumferentially around the lens to retain it so folded while being inserted in the eye, said retainer comprising a band of pliant severable material, said band having opposite circumferential edges, said retainer surrounding the lens with said edges transverse to said axis of folding, said retainer being severable to permit the lens to be unfolded within the eye, said retainer having a pull strip attached to it for withdrawing the retainer from the eye after the retainer has been severed and the lens has been released from it.

* * * * *